(12) United States Patent
Delcayre

(10) Patent No.: US 6,716,430 B2
(45) Date of Patent: Apr. 6, 2004

(54) **COMPOSITIONS ISOLATED FROM *M. VACCAE* AND THEIR USE IN THE MODULATION OF IMMUNE RESPONSES**

(75) Inventor: Alain Delcayre, San Jose, CA (US)

(73) Assignee: Genesis Research and Development Corporation Limited, Parnell (NZ)

( * ) Notice: Subject to any disclaimer, the term of this patent is extended or adjusted under 35 U.S.C. 154(b) by 2 days.

(21) Appl. No.: 10/051,325

(22) Filed: Jan. 18, 2002

(65) Prior Publication Data

US 2002/0168380 A1 Nov. 14, 2002

Related U.S. Application Data

(63) Continuation-in-part of application No. 09/455,960, filed on Dec. 6, 1999, now Pat. No. 6,361,776.

(51) Int. Cl.$^7$ .................. A61K 39/02; A61K 39/04; A61K 39/00; A61K 39/38
(52) U.S. Cl. ................. 424/190.1; 424/184.1; 424/185.1; 424/192.1; 424/234.1; 424/248.1; 435/253.1; 435/320.1; 530/300; 530/350
(58) Field of Search .................. 424/184.1, 185.1, 424/190.1, 192.1, 234.1, 248.1; 435/253.1, 320.1; 530/300, 350

*Primary Examiner*—Rodney P Swartz
(74) *Attorney, Agent, or Firm*—Janet Sheath; Ann W. Speckman

(57) ABSTRACT

Polypeptides and polynucleotides isolated from *Mycobacterium vaccae* are provided, together with compositions comprising such polypeptide and polynucleotides, and methods for their use in the enhancement of immune responses to heterologous antigens.

11 Claims, 6 Drawing Sheets

A

B

```
                         SEQUENCE LISTING

<160> NUMBER OF SEQ ID NOS: 31

<210> SEQ ID NO 1
<211> LENGTH: 402
<212> TYPE: DNA
<213> ORGANISM: Mycobacterium vaccae

<400> SEQUENCE: 1
atcatcggcg gggggttcgg cggattgttc tgcgcccgcc ggctggcccg cagtgcggtg     60
gacgtcatca tgctggatcg ttcggcgggg cacctgttcc agccgctgct ctatcagtgc    120
gcgacgggga cgctgagcat cgcgcacatc agtcgccccc tgcgcgagga gttcgcccgg    180
taccccaaca tcaggacgct gctcggcaag gcggtcgaga tcgaccccga ccgccgggtg    240
gtgaccgcga tgagaccgga cgaatccacg ttcacgctcg actacgacgt gctcgtcgtc    300
gccgccggca tgcagcagtc ctatttcggc aagcgtcatt tcgcggagtg ggcgccaggg    360
atgaagaccc tcgacgacgc gctgggcatc cggcagcgga tc                       402

<210> SEQ ID NO 2
<211> LENGTH: 2500
<212> TYPE: DNA
<213> ORGANISM: Mycobacterium vaccae

<400> SEQUENCE: 2
gatcgccgcg cagtcggccg ccggcgccga gctggcctcc ggggtcggca ctctcgacga     60
tccgcgcgcc ggcgaggatc cgcaggccgc cgcactggcc gcatggtccc tggcgcacgg    120
cttcgcgatg ctgtggctca acaaggccgt cgccaccgac gccgacccgg tcgccaccgc    180
cgaacgggtg gcgcgcatgc tgttcacccc gaaccggccg gccgggaccc ccgacgagta    240
gcgtcggcgt catgactgac gctgcgatca ccgacatccc gctcaccacc ctggacggcc    300
ggcccaccac gctcgcggag ttggccgacg gcgccgcgct ggtggtcaat gtcgcctcca    360
aatgcggtct gacaccgcag tacacggcgc tcgaacagct cgcgaaggac taccgtgaac    420
gcggactcac cgtgatcggc gtgccgtgca accagttcat ggggcaggag cccgggaccg    480
```

-continued

| | |
|---|---|
| ccgaggagat ccagacgttc tgctcgacga cctacgacgt gacgttcccg ctgctggaga | 540 |
| agaccgacgt caacgggccc ggcaggcatc cgctctacgc cgagctggcc cgcgccaccg | 600 |
| acgaggacgc cgaggccggc gacgtgcagt ggaacttcga gaagttcctg ctcgccccgg | 660 |
| gcggcaaagt ggtcaggcgt ttccgtcccc gcaccgcccc ggacgccccc gaggtgatct | 720 |
| cggccatcga agacgtcttg ccccgatagc cgaagcgaca cctgggcgcg cggtgtcgtc | 780 |
| cacctccagg acatatcgcg ttgcgacact tcggtggtgg caggacagct gatcgtgtcg | 840 |
| atctccggaa tcagtgaccg gaccctcggt gaggtcgccg agttccggag tgcgctcgac | 900 |
| gtccgtggcg tgccggtgtc gttcctcgtc gcgccgcgtc tcaagggcgg gtaccggctg | 960 |
| gaccgggacg cggccaccgt cgactggctg atcgaccggc gccggcgcgg cgatgccgtc | 1020 |
| gtgctgcacg gtttcgacga ggcccggacc acagcgcgcc gcggtgagtt cgcgacgctg | 1080 |
| cccgcgcacg aggcgaacct cgcgcctgat gccgccgaca ggatcatgga gcacctggac | 1140 |
| ctgcgcaccc ggatcttcgc cgcgcccggc tggaacgtct ccccgggtgc actcaaagta | 1200 |
| ctgccccgca atgggtttcg cgtccttgcc gggctggcgg gcatcgtcga cctggtcggt | 1260 |
| gggcacactg tgcgcgcgcg ggtgctcggc atcggcgggg gcttcctcgc cgaaccgtgg | 1320 |
| tggtgccgga cgctggtgct ggccgccgaa cgcacggcac gccgcggcgg aaccgtgcgg | 1380 |
| ctgacggtgt cggcccggca gctgagccgc ccgggtcccc ggcaaaccct gctcgacgcc | 1440 |
| gtcgaactgg cgatgctgca ctcgggcgcg gccacggtct accggtggca ccccgaatct | 1500 |
| gcgctgaccg aggccgctta gcggccctcg ctgactacat tggcctgatg gctgatgtca | 1560 |
| tcgttggtgg gcgccgggct ggctggtctg gtcgcagcgt gcgagctggc cgagcgcggc | 1620 |
| cgaagcgtgg ttgactacat tggcctgatg gctgatgtca tcgttggtgg gcgccgggct | 1680 |
| ggctggtctg gtcgcagcgt gcgagctggc cgagcgcggc cgaagcgtgg tgatcgtcga | 1740 |
| ccaggagaac gcggccaatg tcggcggcca ggcgttctgg tcgttcggcg ggctgttctt | 1800 |
| cgtcgacagc ccggagcagc ggcgcatggg catccgggac agtcacgagc tcgcgctgca | 1860 |
| ggactggctc ggctcggccg ggttcgaccg gcccgaggac cactggccgc ggctgtgggc | 1920 |
| ccacgcctac gtcgacttcg ccgccggcga aagcgcagc tggctgcgcg agcgcggtct | 1980 |
| gcagaccttc gcgctggtcg gctgggccga acgcggcgg tacggggcca acgggcacgg | 2040 |
| caactcggtg ccgcgcttcc acatcacgtg gggcaccggg cccgcgctgg tcgacatctt | 2100 |
| cgcgcggcgg ttgaccgggg tgccgcgggt gcggttcgtc caccggcacc gggtggacga | 2160 |
| gctgatcgtc gaggacggtg cggtggtcgg ggtgcgcgga gccgtactgg aaccgtcgtc | 2220 |
| ggcggtaccc ggtgcggaat cctcccgcga ggtcgtcggc gacttcgaga tgcgggcgca | 2280 |
| ggcggtgatc gtggccagcg gcgggatcgg gggcaaccac gacctggtgc gcaaatactg | 2340 |
| gcccaagcga atgggacggg tgcccgaaca actgctcagc ggtgtgcccg cgcacgtcga | 2400 |
| cggacgcatg ctgcagatct cggagaccgc gggtgccagc gtcatcaaca aagaccggat | 2460 |
| gtggcactac accgagggca tcaccaacta cgacccgatc | 2500 |

<210> SEQ ID NO 3
<211> LENGTH: 498
<212> TYPE: DNA
<213> ORGANISM: Mycobacterium vaccae

<400> SEQUENCE: 3

| | |
|---|---|
| atgactgacg ctgcgatcac cgacatcccg ctcaccaccc tggacggccg gcccaccacg | 60 |
| ctcgcggagt tggccgacgg cgccgcgctg gtggtcaatg tcgcctccaa atgcggtctg | 120 |

```
acaccgcagt acacggcgct cgaacagctc gcgaaggact accgtgaacg cggactcacc    180
gtgatcggcg tgccgtgcaa ccagttcatg gggcaggagc ccgggaccgc cgaggagatc    240
cagacgttct gctcgacgac ctacgacgtg acgttcccgc tgctggagaa gaccgacgtc    300
aacgggcccg gcaggcatcc gctctacgcc gagctggccc gcgccaccga cgaggacggc    360
gaggccggcg acgtgcagtg gaacttcgag aagttcctgc tcgccccggg cggcaaagtg    420
gtcaggcgtt tccgtccccg caccgccccg gacgccccg aggtgatctc ggccatcgaa    480
gacgtcttgc cccgatag                                                 498

<210> SEQ ID NO 4
<211> LENGTH: 687
<212> TYPE: DNA
<213> ORGANISM: Mycobacterium vaccae

<400> SEQUENCE: 4
gtgtcgatct ccggaatcag tgaccggacc ctcggtgagg tcgccgagtt ccggagtgcg     60
ctcgacgtcc gtggcgtgcc ggtgtcgttc ctcgtcgcgc gcgtctcaa gggcgggtac    120 cggctggacc gggacgcggc caccgtcgac tggctgatcg accggcgccg gcgcggcgat    180
gccgtcgtgc tgcacggttt cgacgaggcc cggaccacag cgcgccgcgg tgagttcgcg    240
acgctgcccg cgcacgaggc gaacctgcgc ctgatggccg ccgacaggat catggagcac    300
ctggacctgc gcacccggat cttcgccgcg cccggctgga acgtctcccc gggtgcactc    360
aaagtactgc cccgcaatgg gttcgcgtc cttgccgggc tggcgggcat cgtcgacctg    420
gtcggtgggc acactgtgcg cgcgcggtg ctcggcatcg gcggggcctt cctcgccgaa    480
ccgtggtggt gccggacgct ggtgctggcc gccgaacgca cggcacgccg cggcggaacc    540
gtgcggctga cggtgtcggc ccggcagctg agccgcccgg gtccccggca aaccctgctc    600
gacgccgtcg aactggcgat gctgcactcg gcgcggcca cggtctaccg gtggcaccc    660 gaatctgcgc tgaccgaggc cgcttag                                      687

<210> SEQ ID NO 5
<211> LENGTH: 846
<212> TYPE: DNA
<213> ORGANISM: Mycobacterium vaccae

<400> SEQUENCE: 5
atgtcatcgt tggtgggcgc cgggctggct ggtctggtcg cagcgtgcga gctggccgag     60
cgcggccgaa gcgtggtgat cgtcgaccag gagaacgcgg ccaatgtcgg cggccaggcg    120
ttctggtcgt tcgcgggct gttcttcgtc gacagcccgg agcagcggcg catgggcatc    180
cgggacagtc acgagctcgc gctgcaggac tggctcggct cggccgggtt cgaccggccc    240
gaggaccact ggccgcggct gtgggccac gcctacgtcg acttcgccgc cggcgagaag    300
cgcagctggc tgcgcgagcg cggtctgcag accttcgcgc tggtcggctg gccgaacgc    360 ggcggctacg gggccaacgg gcacggcaac tcggtgcgc gcttccacat cacgtggggc    420
accgggcccg cgctggtcga catcttcgcg cggcggttga ccggggtgcc gcgggtgcgg    480
ttcgtccacc ggcaccgggt ggacgagctg atcgtcgagg acgtgcggt ggtcggggtg    540 cgcggagccg tactggaacc gtcgtcggcg gtacccggtg cggaatcctc ccgcgaggtc    600
gtcggcgact cgagatgcg ggcgcaggcg gtgatcgtgg ccagcggcgg gatcgggggc    660
aaccacgacc tggtgcgcaa atactggccc aagcggatgg gacgggtgcc cgaacaactg    720
```

```
ctcagcggtg tgcccgcgca cgtcgacgga cgcatgctgc agatctcgga gaccgcgggt    780
gccagcgtca tcaacaaaga ccggatgtgg cactacaccg agggcatcac caactacgac    840
ccgatc                                                                846
```

```
<210> SEQ ID NO 6
<211> LENGTH: 134
<212> TYPE: PRT
<213> ORGANISM: Mycobacterium vaccae

<400> SEQUENCE: 6
```

```
Ile Ile Gly Gly Gly Phe Gly Gly Leu Phe Cys Ala Arg Arg Leu Ala
  1               5                  10                  15

Arg Ser Ala Val Asp Val Ile Met Leu Asp Arg Ser Ala Gly His Leu
             20                  25                  30

Phe Gln Pro Leu Leu Tyr Gln Cys Ala Thr Gly Thr Leu Ser Ile Ala
         35                  40                  45

His Ile Ser Arg Pro Leu Arg Glu Glu Phe Ala Arg Tyr Pro Asn Ile
     50                  55                  60

Arg Thr Leu Leu Gly Lys Ala Val Glu Ile Asp Pro Asp Arg Arg Val
 65                  70                  75                  80

Val Thr Ala Met Arg Pro Asp Glu Ser Thr Phe Thr Leu Asp Tyr Asp
                 85                  90                  95

Val Leu Val Val Ala Ala Gly Met Gln Gln Ser Tyr Phe Gly Lys Arg
            100                 105                 110

His Phe Ala Glu Trp Ala Pro Gly Met Lys Thr Leu Asp Asp Ala Leu
        115                 120                 125

Gly Ile Arg Gln Arg Ile
    130
```

```
<210> SEQ ID NO 7
<211> LENGTH: 165
<212> TYPE: PRT
<213> ORGANISM: Mycobacterium vaccae

<400> SEQUENCE: 7
```

```
Met Thr Asp Ala Ala Ile Thr Asp Ile Pro Leu Thr Thr Leu Asp Gly
  1               5                  10                  15

Arg Pro Thr Thr Leu Ala Glu Leu Ala Asp Gly Ala Ala Leu Val Val
             20                  25                  30

Asn Val Ala Ser Lys Cys Gly Leu Thr Pro Gln Tyr Thr Ala Leu Glu
         35                  40                  45

Gln Leu Ala Lys Asp Tyr Arg Glu Arg Gly Leu Thr Val Ile Gly Val
     50                  55                  60

Pro Cys Asn Gln Phe Met Gly Gln Glu Pro Gly Thr Ala Glu Glu Ile
 65                  70                  75                  80

Gln Thr Phe Cys Ser Thr Thr Tyr Asp Val Thr Phe Pro Leu Leu Glu
                 85                  90                  95

Lys Thr Asp Val Asn Gly Pro Gly Arg His Pro Leu Tyr Ala Glu Leu
            100                 105                 110

Ala Arg Ala Thr Asp Glu Asp Gly Glu Ala Gly Asp Val Gln Trp Asn
        115                 120                 125

Phe Glu Lys Phe Leu Leu Ala Pro Gly Gly Lys Val Val Arg Arg Phe
    130                 135                 140

Arg Pro Arg Thr Ala Pro Asp Ala Pro Glu Val Ile Ser Ala Ile Glu
145                 150                 155                 160
```

-continued

```
Asp Val Leu Pro Arg
                165

<210> SEQ ID NO 8
<211> LENGTH: 228
<212> TYPE: PRT
<213> ORGANISM: Mycobacterium vaccae

<400> SEQUENCE: 8

Val Ser Ile Ser Gly Ile Ser Asp Arg Thr Leu Gly Glu Val Ala Glu
 1               5                  10                  15

Phe Arg Ser Ala Leu Asp Val Arg Gly Val Pro Val Ser Phe Leu Val
            20                  25                  30

Ala Pro Arg Leu Lys Gly Gly Tyr Arg Leu Asp Arg Asp Ala Ala Thr
        35                  40                  45

Val Asp Trp Leu Ile Asp Arg Arg Arg Arg Gly Asp Ala Val Val Leu
    50                  55                  60

His Gly Phe Asp Glu Ala Arg Thr Thr Ala Arg Arg Gly Glu Phe Ala
65                  70                  75                  80

Thr Leu Pro Ala His Glu Ala Asn Leu Arg Leu Met Ala Ala Asp Arg
                85                  90                  95

Ile Met Glu His Leu Asp Leu Arg Thr Arg Ile Phe Ala Ala Pro Gly
            100                 105                 110

Trp Asn Val Ser Pro Gly Ala Leu Lys Val Leu Pro Arg Asn Gly Phe
        115                 120                 125

Arg Val Leu Ala Gly Leu Ala Gly Ile Val Asp Leu Val Gly Gly His
    130                 135                 140

Thr Val Arg Ala Arg Val Leu Gly Ile Gly Gly Gly Phe Leu Ala Glu
145                 150                 155                 160

Pro Trp Trp Cys Arg Thr Leu Val Leu Ala Ala Glu Arg Thr Ala Arg
                165                 170                 175

Arg Gly Gly Thr Val Arg Leu Thr Val Ser Ala Arg Gln Leu Ser Arg
            180                 185                 190

Pro Gly Pro Arg Gln Thr Leu Leu Asp Ala Val Glu Leu Ala Met Leu
        195                 200                 205

His Ser Gly Ala Ala Thr Val Tyr Arg Trp His Pro Glu Ser Ala Leu
    210                 215                 220

Thr Glu Ala Ala
225

<210> SEQ ID NO 9
<211> LENGTH: 282
<212> TYPE: PRT
<213> ORGANISM: Mycobacterium vaccae

<400> SEQUENCE: 9

Met Ser Ser Leu Val Gly Ala Gly Leu Ala Gly Leu Val Ala Ala Cys
 1               5                  10                  15

Glu Leu Ala Glu Arg Gly Arg Ser Val Val Ile Val Asp Gln Glu Asn
            20                  25                  30

Ala Ala Asn Val Gly Gly Gln Ala Phe Trp Ser Phe Gly Gly Leu Phe
        35                  40                  45

Phe Val Asp Ser Pro Glu Gln Arg Arg Met Gly Ile Arg Asp Ser His
    50                  55                  60

Glu Leu Ala Leu Gln Asp Trp Leu Gly Ser Ala Gly Phe Asp Arg Pro
65                  70                  75                  80
```

Glu Asp His Trp Pro Arg Leu Trp Ala His Ala Tyr Val Asp Phe Ala
            85                  90                  95

Ala Gly Glu Lys Arg Ser Trp Leu Arg Glu Arg Gly Leu Gln Thr Phe
       100                 105                 110

Ala Leu Val Gly Trp Ala Glu Arg Gly Gly Tyr Gly Ala Asn Gly His
       115                 120                 125

Gly Asn Ser Val Pro Arg Phe His Ile Thr Trp Gly Thr Gly Pro Ala
       130                 135                 140

Leu Val Asp Ile Phe Ala Arg Arg Leu Thr Gly Val Pro Arg Val Arg
145                 150                 155                 160

Phe Val His Arg His Arg Val Asp Glu Leu Ile Val Glu Asp Gly Ala
                165                 170                 175

Val Val Gly Val Arg Gly Ala Val Leu Glu Pro Ser Ser Ala Val Pro
            180                 185                 190

Gly Ala Glu Ser Ser Arg Glu Val Val Gly Asp Phe Glu Met Arg Ala
        195                 200                 205

Gln Ala Val Ile Val Ala Ser Gly Gly Ile Gly Gly Asn His Asp Leu
    210                 215                 220

Val Arg Lys Tyr Trp Pro Lys Arg Met Gly Arg Val Pro Glu Gln Leu
225                 230                 235                 240

Leu Ser Gly Val Pro Ala His Val Asp Gly Arg Met Leu Gln Ile Ser
                245                 250                 255

Glu Thr Ala Gly Ala Ser Val Ile Asn Lys Asp Arg Met Trp His Tyr
            260                 265                 270

Thr Glu Gly Ile Thr Asn Tyr Asp Pro Ile
        275                 280

<210> SEQ ID NO 10
<211> LENGTH: 242
<212> TYPE: DNA
<213> ORGANISM: Mycobacterium vaccae

<400> SEQUENCE: 10
tcgaacgagg ggcgtgaccc ggtgcggggc ttcttgcact cggcataggc gagtgctaag      60
aataacgttg gcactcgcga ccggtgagtg ctaggtcggg acggtgaggc caggcccgtc     120
gtcgcagcga gtggcagcga ggacaacttg agccgtccgt cgcgggcact gcgcccggcc     180
agcgtaagta gcggggttgc cgtcacccgg tgaccccgt ttcatccccg atccggagga     240
at                                                                    242

<210> SEQ ID NO 11
<211> LENGTH: 47
<212> TYPE: DNA
<213> ORGANISM: Mycobacterium vaccae

<400> SEQUENCE: 11
gaagaagagg atccgatatc aagcttcatc accatcacca tcacctg                    47

<210> SEQ ID NO 12
<211> LENGTH: 36
<212> TYPE: DNA
<213> ORGANISM: Mycobacterium vaccae

<400> SEQUENCE: 12
gagagagaga tcgattcagt gatggtgatg gtgatg                                36

<210> SEQ ID NO 13

-continued

```
<210> SEQ ID NO 13
<211> LENGTH: 36
<212> TYPE: DNA
<213> ORGANISM: Mycobacterium vaccae

<400> SEQUENCE: 13
gaagaaggag tctagatcga acgaggggcg tgaccc                    36

<210> SEQ ID NO 14
<211> LENGTH: 47
<212> TYPE: DNA
<213> ORGANISM: Mycobacterium vaccae

<400> SEQUENCE: 14
gagagagagg atccgcccgg gctgcagatt cctccggatc ggggatg        47

<210> SEQ ID NO 15
<211> LENGTH: 42
<212> TYPE: DNA
<213> ORGANISM: Mycobacterium vaccae

<400> SEQUENCE: 15
gatccgatat caagcttcat caccatcacc atcactgaat cg             42

<210> SEQ ID NO 16
<211> LENGTH: 34
<212> TYPE: DNA
<213> ORGANISM: Mycobacterium vaccae

<400> SEQUENCE: 16
gagagagaag cttgatccgc tgccggatgc ccag                      34

<210> SEQ ID NO 17
<211> LENGTH: 24
<212> TYPE: DNA
<213> ORGANISM: Mycobacterium vaccae

<400> SEQUENCE: 17
atgatcatcg gcggggggtt cggc                                 24

<210> SEQ ID NO 18
<211> LENGTH: 24
<212> TYPE: DNA
<213> ORGANISM: Mycobacterium vaccae

<400> SEQUENCE: 18
atgcatcggc gggggttcg gcgg                                  24

<210> SEQ ID NO 19
<211> LENGTH: 21
<212> TYPE: DNA
<213> ORGANISM: Mycobacterium vaccae

<400> SEQUENCE: 19
atgactgacg ctgcgatcac c                                    21

<210> SEQ ID NO 20
<211> LENGTH: 36
<212> TYPE: DNA
<213> ORGANISM: Mycobacterium vaccae

<400> SEQUENCE: 20
gagagagaag ctttcggggc aagacgtctt cgatgg                    36
```

-continued

<210> SEQ ID NO 21
<211> LENGTH: 22
<212> TYPE: DNA
<213> ORGANISM: Mycobacterium vaccae

<400> SEQUENCE: 21
atgtcgatct ccggaatcag tg                                              22

<210> SEQ ID NO 22
<211> LENGTH: 37
<212> TYPE: DNA
<213> ORGANISM: Mycobacterium vaccae

<400> SEQUENCE: 22
gagagagaag cttagcggcc tcggtcagcg cagattc                              37

<210> SEQ ID NO 23
<211> LENGTH: 21
<212> TYPE: DNA
<213> ORGANISM: Mycobacterium vaccae

<400> SEQUENCE: 23
atgtcatcgt tggtgggcgc c                                               21

<210> SEQ ID NO 24
<211> LENGTH: 37
<212> TYPE: DNA
<213> ORGANISM: Mycobacterium vaccae

<400> SEQUENCE: 24
gagagagaag cttgatcggg tcgtagttgg tgatgcc                              37

<210> SEQ ID NO 25
<211> LENGTH: 36
<212> TYPE: DNA
<213> ORGANISM: Mycobacterium vaccae

<400> SEQUENCE: 25
gagagagaga attcgctgga tcgttcggcg gggcac                               36

<210> SEQ ID NO 26
<211> LENGTH: 37
<212> TYPE: DNA
<213> ORGANISM: Mycobacterium vaccae

<400> SEQUENCE: 26
ggaaggaagg atcctagatc cgctgccgga tgcccag                              37

<210> SEQ ID NO 27
<211> LENGTH: 36
<212> TYPE: DNA
<213> ORGANISM: Mycobacterium vaccae

<400> SEQUENCE: 27
gagagagaga attcgactga cgctgcgatc accgac                               36

<210> SEQ ID NO 28
<211> LENGTH: 35
<212> TYPE: DNA
<213> ORGANISM: Mycobacterium vaccae

<400> SEQUENCE: 28
ggaaggaagg atcctatcgg ggcaagacgt cttcg                                35

```
<210> SEQ ID NO 29
<211> LENGTH: 39
<212> TYPE: DNA
<213> ORGANISM: Mycobacterium vaccae

<400> SEQUENCE: 29
gagagagaga attcgtcgat ctccggaatc agtgaccgg                    39

<210> SEQ ID NO 30
<211> LENGTH: 36
<212> TYPE: DNA
<213> ORGANISM: Mycobacterium vaccae

<400> SEQUENCE: 30
ggaaggaagg atcctaagcg gcctcggtca gcgcag                       36

<210> SEQ ID NO 31
<211> LENGTH: 17
<212> TYPE: PRT
<213> ORGANISM: Mycobacterium vaccae

<400> SEQUENCE: 31

Ile Ser Gln Ala Val His Ala Ala His Ala Glu Ile Asn Glu Ala Gly
1               5                   10                  15
Arg
```

COMPOSITIONS ISOLATED FROM M. VACCAE AND THEIR USE IN THE MODULATION OF IMMUNE RESPONSES

REFERENCE TO RELATED APPLICATIONS

This application is a continuation-in-part of U.S. patent application Ser. No. 09/455,960, filed Dec. 6, 1999, now U.S. Pat. No. 6,361,776.

TECHNICAL FIELD

The present invention relates generally to compositions for modulating immune responses. In certain embodiments, the invention is related to polypeptides and polynucleotides isolated from Mycobacterium vaccae and their use in the enhancement of immune responses to heterologous antigens.

BACKGROUND OF THE INVENTION

Mycobacterium vaccae (M. vaccae) is a mycobacterium that is non-pathogenic in humans and that has been used for immunotherapy of tuberculosis and also leprosy. M. vaccae is believed to contain antigenic compounds that are recognized by the immune system of individuals exposed to infection with M. tuberculosis and other infectious and/or inflammatory disorders.

Several patents and other publications disclose treatment of various conditions by administering mycobacteria, including M. vaccae, or certain mycobacterial fractions. U.S. Pat. No. 4,716,038 discloses diagnosis of, vaccination against and treatment of autoimmune diseases of various types, including arthritic diseases, by administering mycobacteria, including M. vaccae. U.S. Pat. No. 4,724,144 discloses an immunotherapeutic agent comprising antigenic material derived from M. vaccae for treatment of mycobacterial diseases, especially tuberculosis and leprosy, and as an adjuvant to chemotherapy. International Patent Publication WO 91/01751 discloses the use of antigenic and/or immunoregulatory material from M. vaccae as an immunoprophylactic to delay and/or prevent the onset of AIDS. International Patent Publication WO 94/06466 discloses the use of antigenic and/or immunoregulatory material derived from M. vaccae for therapy of HIV infection, with or without AIDS and with or without associated tuberculosis.

In addition to being antigenic, M. vaccae has immunogenic properties. U.S. Pat. No. 5,599,545 discloses the use of mycobacteria, especially whole, inactivated M. vaccae, as an adjuvant for administration with antigens which are not endogenous to M. vaccae. This publication theorizes that the beneficial effect as an adjuvant may be due to heat shock protein 65 (HSP65). International Patent Publication WO 92/08484 discloses the use of antigenic and/or immunoregulatory material derived from M. vaccae for the treatment of uveitis. International Patent Publication WO 93/16727 discloses the use of antigenic and/or immunoregulatory material derived from M. vaccae for the treatment of mental diseases associated with an autoimmune reaction initiated by an infection. International Patent Publication WO 95/26742 discloses the use of antigenic and/or immunoregulatory material derived from M. vaccae for delaying or preventing the growth or spread of tumors. International Patent Publication WO 91/02542 discloses the use of autoclaved M. vaccae in the treatment of chronic inflammatory disorders in which a patient demonstrates an abnormally high release of IL-6 and/or TNF or in which the patient's IgG shows an abnormally high proportion of agalactosyl IgG. Among the disorders mentioned in this publication are psoriasis, rheumatoid arthritis, mycobacterial disease, Crohn's disease, primary biliary cirrhosis, sarcoidosis, ulcerative colitis, systemic lupus erythematosus, multiple sclerosis, Guillain-Barre syndrome, primary diabetes mellitus, and some aspects of graft rejection.

M. vaccae is apparently unique among known mycobacterial species in that heat-killed preparations retain vaccine and immunotherapeutic properties. Heat-killed M. bovis BCG and M. tuberculosis have no protective properties when employed in vaccines. For example, M. tuberculosis BCG vaccines, used for vaccination against tuberculosis, employ live strains. A number of compounds have been isolated from a range of mycobacterial species which have adjuvant properties. The effect of such adjuvants is essentially to stimulate a particular immune response mechanism against an antigen from another species.

Certain pathogens, such as M. tuberculosis, as well as certain cancers, are effectively contained by an immune attack directed by $CD4^+$ T cells, known as cell-mediated immunity. Other pathogens, such as poliovirus, also require antibodies, produced by B cells, for containment. These different classes of immune attack (T cell or B cell) are controlled by different subpopulations of $CD4^+$ T cells, commonly referred to as Th1 and Th2 cells.

The two types of Th cell subsets have been well characterized in a murine model and are defined by the cytokines they release upon activation. The Th1 subset secretes IL-2, IFN-γ and tumor necrosis factor, and mediates macrophage activation and delayed-type hypersensitivity response. The Th2 subset releases IL4, IL-5, IL-6 and IL-10, which stimulate B cell activation. The Th1 and Th2 subsets are mutually inhibiting. For example, IL-4 inhibits Th1-type responses, and IFN-γ inhibits Th2-type responses. Similar Th1 and Th2 subsets have been found in humans, with release of cytokines identical to those observed in the murine model. Amplification of Th2-type immune responses is central to protecting against metazoan parasites, e.g. Schistosoma and Leishmania. In addition, a Th2-type response is important in the induction and maintenance of allograft tolerance and the maintenance of successful pregnancy. In contrast, suppression of a Th2-type response and amplification of a Th1-type immune response is of key importance in the treatment of diseases including cancers and disorders of the respiratory system, such as tuberculosis, sarcoidosis, asthma, allergic rhinitis and lung cancers.

Asthma is a common disease, with a high prevalence in the developed world. Asthma is characterized by increased responsiveness of the tracheobronchial tree to a variety of stimuli, the primary physiological disturbance being reversible airflow limitation, which may be spontaneous or drug-related, and the pathological hallmark being inflammation of the airways. The immune response producing airway inflammation in asthma is brought about by the Th2 class of T cells which secrete IL-4, IL5 and IL-10. It has been shown that lymphocytes from the lungs of atopic asthmatic patients produce IL-4 and L-5 when activated. Both IL-4 and IL-5 are cytokines of the Th2 class and are required for the production of IgE and involvement of eosinophils in asthma. Thus reversal of a Th2 response and enhancement of a Th1 response is highly beneficial in the treatment of asthma.

Another disorder with a similar immune abnormality to asthma is allergic rhinitis. Allergic rhinitis is a common disorder and is estimated to affect at least 10% of the population. Allergic rhinitis may be seasonal (hay fever) and caused by allergy to pollen. Non-seasonal (perennial) rhinitis is caused by allergy to antigens such as those from house dust mite or animal dander. The abnormal immune response in allergic rhinitis is characterized by the excess production of IgE antibodies specific against the allergen. The inflammatory response occurs in the nasal mucosa rather than further down the airways as in asthma. Like asthma, local eosinophilia in the affected tissues is a major feature of allergic rhinitis. As with asthma, the reversal of a Th2 immune response and enhancement of a Th1 response is central to successful treatment.

SUMMARY OF THE INVENTION

Briefly stated, the present invention provides compositions isolated from *Mycobacterium vaccae* (*M. vaccae*), together with methods for their use in eliciting and/or enhancing an immune response to a heterologous antigen. In a first aspect, isolated polypeptides derived from *M. vaccae* are provided, together with variants of such polypeptides. In one embodiment, the inventive polypeptides include an amino acid sequence selected from the group consisting of: (a) sequences recited in SEQ ID NO: 6–9; (b) sequences having at least about 65% identity to a sequence recited in SEQ ID NO: 6–9; (c) sequences having at least about 75% identity to a sequence recited in SEQ ID NO: 6–9; (d) sequences having at least about 90% identity to a sequence recited in SEQ ID NO: 6–9; and (e) sequences having at least about 95% identity to a sequence recited in SEQ ID NO: 6–9, as measured using alignments produced by the computer algorithm BLASTP.

Polynucleotides encoding the inventive polypeptides, expression vectors comprising such polynucleotides, and host cells transformed or transfected with such expression vectors are also provided. In another aspect, the present invention provides fusion proteins comprising at least one polypeptide of the present invention. The invention also provides vaccines comprising at least one of the above polypeptides, polynucleotides and a heterologous antigen. In certain embodiments, the heterologous antigen is selected from the group consisting of: tumor-specific antigens, infectious disease antigens and autoantigens.

In yet another aspect, methods are provided for enhancing an immune response in a patient, comprising administering to a patient an effective amount of one or more of the above vaccines. In specific embodiments, the immune response is a Th1 or Th2 response.

In further aspects of this invention, methods are provided for the treatment of a disorder in a patient, comprising administering to the patient a vaccine of the present invention. In certain embodiments, the disorder is characterized by the presence of a Th2 immune response. Examples of such disorders include sarcoidosis, asthma, allergic rhinitis, chronic graft versus host disease, systemic lupus erythematosus, systemic sclerosis and cancer. In other embodiments, the disorder is characterized by the presence of a Th1 immune response. Examples of Th1-type disorders include tuberculosis, autoimmune thyroiditis, insulin-dependent diabetes mellitus, multiple sclerosis, Crohn's disease, *Helicobacter pyloris*-induced peptic ulcers, transplanted organ rejection and unexplained recurrent naturally-occurring abortions.

These and other aspects of the present invention will become apparent upon reference to the following detailed description and attached drawings. All references disclosed herein are hereby incorporated by reference in their entirety as if each was incorporated individually.

DETAILED DESCRIPTION OF THE INVENTION

Figure 1:
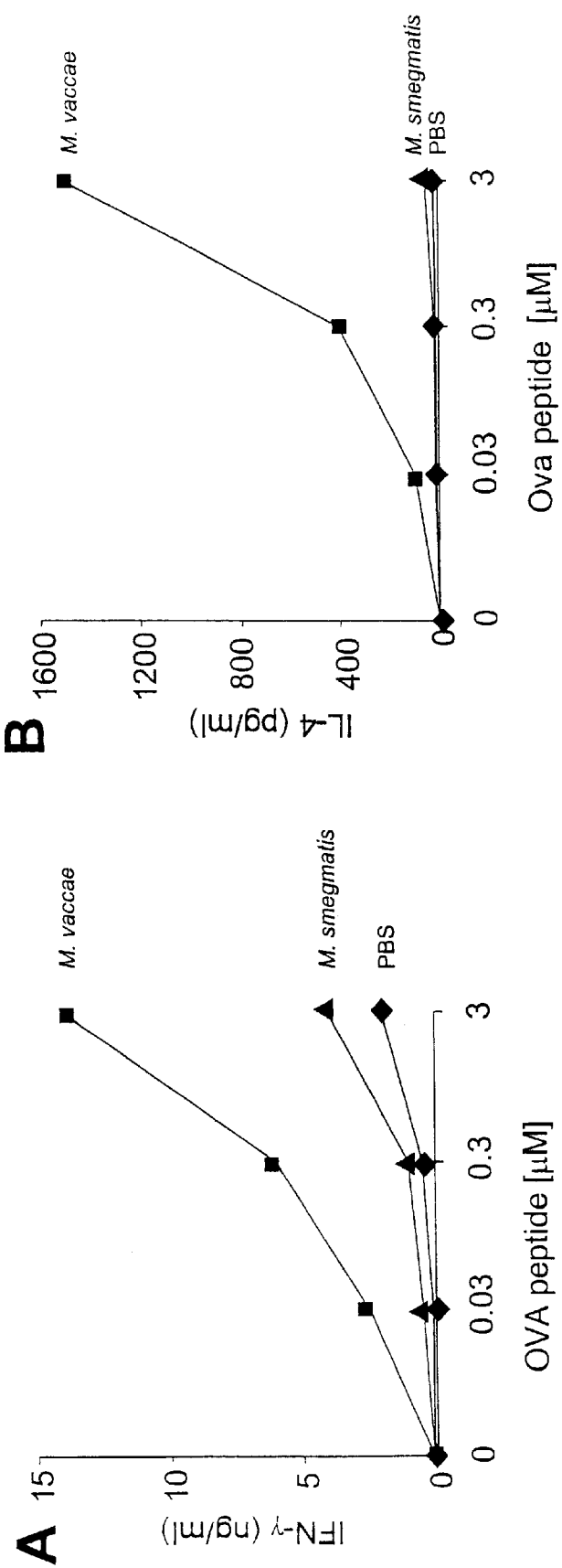
FIGS. 1A and B illustrate the production of IFN-γ (FIG. 1A) and IL-4 (FIG. 1B) by OVA-TCR transgenic mice immunized with either OVA and heat-killed *M. vaccae* or OVA and heat-killed *M. smegmatis*. Control mice were immunized with OVA plus PBS.

As noted above, the present invention is generally directed to polynucleotides and polypeptides isolated from *M. vaccae* that act as immunostimulants and their use in combination with known heterologous antigens in the treatment of immunologically-mediated disorders. Disorders that may be usefully treated using the compositions of the present invention include microbial infections, cancers, autoimmune diseases, inflammatory disorders, allograft rejection, unexplained recurrent naturally-occurring abortions and peptic ulcers.

As used herein, the term "immunostimulant" refers to a component that has the ability to elicit and/or potentiate an immune response to a heterologous antigen. A "Th2 immunostimulant", as used herein, refers to a component that induces an increase in Th2-type cytokine production in T cells and/or induces an increase in the production of antibodies of the type IgG1, thereby eliciting or potentiating a Th2-type immune response. Examples of Th2-type cytokines include IL-4 and IL-5. A "Th1 immunostimulant", as used herein, refers to a component that induces an increase in Th1-type cytokine production in T cells and/or an increase in the production of antibodies of the IgG2a type, thereby eliciting or potentiating a Th1-type immune response. A Th1 immunostimulant thus has the ability to increase the production of cytokines such as IL-2, IFN-γ and tumor necrosis factor.

In one aspect, the present invention provides polypeptides that comprise at least one immunogenic epitope of a *M. vaccae* protein, or a variant thereof. In specific embodiments, the inventive polypeptides comprise a sequence provided in SEQ ID NO: 6–9. As used herein, the term "polypeptide" encompasses amino acid chains of any length, including full-length proteins, wherein the amino acid residues are linked by covalent peptide bonds. Thus, a polypeptide comprising an immunogenic epitope of a protein may consist entirely of the immunogenic epitope, or may contain additional sequences. The additional sequences may be derived from the native *M. vaccae* protein or may be heterologous, and such sequences may (but need not) be immunogenic.

"Immunogenic," as used herein, refers to the ability to elicit or potentiate an immune response in a patient, such as a human, or in a biological sample. In particular, an immunogenic epitope is that portion of a polypeptide that is capable of stimulating cell proliferation, interleukin-12 production or interferon-γ or IL-4 production in biological samples comprising one or more cells selected from the group of T cells, NK cells, B cells and macrophages, where the cells are derived from a mycobacteria-immune individual.

In another aspect, the present invention provides isolated polynucleotides that encode an inventive polypeptide. In specific embodiments, the inventive polynucleotides comprise a sequence of SEQ ID NO: 1–5. Complements of the inventive isolated polynucleotides, reverse complements of such isolated polynucleotides and reverse sequences of such isolated polynucleotides are also provided, together with variants of such sequences. The present invention also encompasses polynucleotide sequences that differ from the disclosed sequences but which, due to the degeneracy of the genetic code, encode a polypeptide which is the same as that encoded by a polynucleotide sequence disclosed herein.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and/or DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments. Anti-sense polynucleotides and techniques involving anti-sense polynucleotides are well known in the art and are described, for example, in Robinson-Benion et al. "Antisense techniques," *Methods in Enzymol.* 254:363–375, 1995; and Kawasaki et al. *Artific. Organs* 20:836–848, 1996.

The definition of the terms "complement", "reverse complement" and "reverse sequence", as used herein, is best illustrated by the following example. For the sequence 5' AGGACC 3', the complement, reverse complement and reverse sequence are as follows:

```
complement          3' TCCTGG 5'
reverse complement  3' GGTCCT 5'
reverse sequence    5' CCAGGA 3'.
```

All of the polynucleotides and polypeptides described herein are isolated and purified, as those terms are commonly used in the art. Preferably, the polypeptides and polynucleotides are at least about 80% pure, more preferably at least about 90% pure, and most preferably at least about 99% pure.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. In certain embodiments, variants of the inventive sequences retain certain, or all, of the functional characteristics of the inventive sequence. Preferably such variants are capable of eliciting and/or enhancing an immune response. Variant sequences (polynucleotide or polypeptide) preferably exhibit at least 55%, more preferably at least 65%, more preferably at least 75%, more preferably yet at least 90%, and most preferably at least 95% identity to a sequence of the present invention. The percentage identity is determined by aligning the two sequences to be compared, determining the number of identical residues in the aligned portion, dividing that number by the total length of the inventive, or queried, sequence and multiplying the result by 100.

Polynucleotide or polypeptide sequences may be aligned, and percentage of identical residues in a specified region may be determined against another polynucleotide, using computer algorithms that are publicly available. Two exemplary algorithms for aligning and identifying the similarity of polynucleotide sequences are the BLASTN and FASTA algorithms. Polynucleotides may also be analyzed using the BLASTX algorithm, which compares the six-frame conceptual translation products of a nucleotide query sequence (both strands) against a protein sequence database. The similarity of polypeptide sequences may be examined using the BLASTP or FASTX algorithms. Both the BLASTN and BLASTP software are available on the NCBI anonymous FTP server under /blast/executables/. The BLASTN algorithm version 2.0.6 [Sep. 16, 1998], set to the default parameters described in the documentation and distributed with the algorithm, is preferred for use in the determination of variants according to the present invention. The use of the BLAST family of algorithms, including BLASTN and BLASTP, is described at NCBI's website and in the publication of Altschul et al., "Gapped BLAST and PSI-BLAST: a new generation of protein database search programs", *Nucleic Acids Res.* 25:3389–3402, 1997. The computer algorithm FASTA is available on the Internet. Version3.1t11, August 1998, set to the default parameters described in the documentation and distributed with the algorithm, is preferred for use in the determination of variants according to the present invention. The use of the FASTA algorithm is described in Pearson and Lipman, "Improved Tools for Biological Sequence Analysis," *Proc. Natl. Acad. Sci. USA* 85:2444–2448, 1988 and Pearson, "Rapid and Sensitive Sequence Comparison with FASTP and FASTA," *Methods in Enzymol.* 183:63–98, 1990. The use of the FASTX algorithm is described in Pearson et al., "Comparison of DNA sequences with protein sequences," *Genomics* 46:24–36, 1997.

The following running parameters are preferred for determination of alignments and similarities using BLASTN that contribute to the E values and percentage identity: Unix running command: blastall -p blastn -d embldb -e 10-G 0-E 0-r 1-v 30-b 30-i queryseq -o results; and parameter default values:

-p Program Name [String]

-d Database [String]

-e Expectation value (E) [Real]
-G Cost to open a gap (zero invokes default behavior) [Integer]
-E Cost to extend a gap (zero invokes default behavior) [Integer]
-r Reward for a nucleotide match (BLASTN only) [Integer]
-v Number of one-line descriptions (V) [Integer]
-b Number of alignments to show (B) [Integer]
-i Query File [File In]
-o BLAST report Output File [File Out] Optional For BLASTP the following running parameters are preferred: blastall -p blastp -d swissprotdb - e 10-G 0-E 0-v 30-b 30-i queryseq -o results -p Program Name [String]
-d Database [String]
-e Expectation value (E) [Real]
-G Cost to open a gap (zero invokes default behavior) [Integer]
-E Cost to extend a gap (zero invokes default behavior) [Integer]
-v Number of one-line descriptions (v) [Integer]
-b Number of alignments to show (b) [Integer]
-I Query File [File In]
-o BLAST report Output File [File Out] Optional The "hits" to one or more database sequences by a queried sequence produced by BLASTN, BLASTP, FASTA or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN and FASTA algorithms also produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a hit is interpreted as meaning that in a database of the size of the EMBL database, one might expect to see 0.1 matches over the aligned portion of the sequence with a similar score simply by chance. By this criterion, the aligned and matched portions of the sequences then have a probability of 90% of being the same. For sequences having an E value of 0.01 or less over aligned and matched portions, the probability of finding a match by chance in the EMBL database is 1% or less using the BLASTN or FASTA algorithm.

According to one embodiment, "variant" polynucleotides comprise sequences having the same number or fewer nucleic acids than each of the polynucleotides of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN or FASTA algorithms set at the default parameters. According to a preferred embodiment, a variant polynucleotide is a sequence having the same number or fewer nucleic acids than a polynucleotide of the present invention that has at least a 99% probability of being the same as the polynucleotide of the present invention, measured as having an E value of 0.01 or less using the BLASTN or FASTA algorithms set at the default parameters.

Alternatively, variant polynucleotide sequences hybridize to the recited polynucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

Thus, polynucleotides comprising sequences that differ from the polynucleotide sequences provided herein, or complements, reverse sequences, or reverse complements thereof, as a result of conservative substitutions are contemplated by and encompassed within the present invention. Polynucleotides comprising sequences that differ from the polynucleotide sequences provided herein (or complements, reverse complements or reverse sequences thereof) as a result of deletions and/or insertions totaling less than 10% of the total sequence length are also contemplated by and encompassed within the present invention. Similarly, polypeptides comprising sequences that differ from the polypeptide sequences provided herein, as a result of amino acid substitutions, insertions, and/or deletions totaling less than 10% of the total sequence length are contemplated by and encompassed within the present invention.

A polypeptide of the present invention may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

As used herein, the term "x-mer," with reference to a specific value of "x," refers to a polynucleotide comprising at least a specified number ("x") of contiguous residues of any of the polynucleotides identified as SEQ ID NO: 1–5. The value of x may be from about 20 to about 600, depending upon the specific sequence.

Polynucleotides of the present invention comprehend polynucleotides comprising at least a specified number of contiguous residues (x-mers) of any of the polynucleotides identified as SEQ ID NO: 1–5 or their variants. According to preferred embodiments, the value of x is preferably at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer a 250-mer, or a 300-mer, 400-mer, 500-mer or 600-mer of a polynucleotide identified as SEQ ID NO: 1–5 or a variant of one of the polynucleotides identified as SEQ ID NO: 1–5.

In general, the inventive polypeptides and polynucleotides, may be prepared using any of a variety of procedures. For example, polypeptides may be produced recombinantly by inserting a polynucleotide that encodes the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a polynucleotide that encodes a recombinant polypeptide. Suitable host cells include prokaryotes, yeast and higher eukaryotic cells.

Preferably, the host cells employed are *E. coli*, mycobacteria, insect, yeast or a mammalian cell line such as COS or CHO. The polynucleotides expressed in this manner may encode naturally occurring proteins, portions of naturally occurring proteins, or other variants thereof.

Polynucleotides of the present invention may be isolated from a *M. vaccae* genomic DNA library as described below. Alternatively, polynucleotides encoding the inventive polypeptides may be obtained by screening an appropriate *M. vaccae* cDNA or genomic DNA library for DNA sequences that hybridize to degenerate oligonucleotides derived from amino acid sequences of isolated epitopes. Suitable degenerate oligonucleotides may be designed and synthesized, and the screen may be performed as described, for example in Sambrook et al., *Molecular cloning: a laboratory manual.* CSHL Press: Cold Spring Harbor, N.Y., 1989. Polymerase chain reaction (PCR) may be employed to isolate a nucleic acid probe from genomic DNA, or a cDNA or genomic DNA library, using techniques well known in the art. The library screen may then be performed using the isolated probe.

Portions and other variants of the inventive polypeptides may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2154, 1963. Equipment for automated synthesis of polypeptides is commercially available from suppliers such as Perkin Elmer/Applied BioSystems, Inc. (Foster City, Calif.), and may be operated according to the manufacturer's instructions. Variants of a native epitope may be prepared using standard mutagenesis techniques, such as oligonucleotide-directed site-specific mutagenesis. Sections of the DNA sequence may also be removed using standard techniques to permit preparation of truncated polypeptides.

The present invention also provides fusion proteins comprising a first and a second inventive polypeptide or, alternatively, a polypeptide of the present invention and a known heterologous antigen, together with variants of such fusion proteins. The fusion proteins of the present invention may also include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may be from 1 to about 50 amino acids in length. Peptide linker sequences are not required when the first and second polypeptides have non-essential N-terminal amino acid regions that can be used to separate the functional domains and prevent steric interference.

The ligated DNA sequences encoding the fusion proteins are cloned into suitable expression systems using techniques known to those of ordinary skill in the art.

Regardless of the method of preparation, the polynucleotides and polypeptides described herein have the ability to enhance an immune response to either an antigen from a different species or to an antigen from the same species that has a different structure to the inventive polypeptide. More specifically, the inventive polynucleotides and polypeptides have the ability to induce cytokine and/or antibody production (either of the Th1-type or Th2-type) in T cells. The ability of a composition to act as either a Th1 immunostimulant or a Th2 immunostimulant may be determined as described below in Example 1.

In another aspect, the present invention provides compositions comprising one or more of the inventive polypeptides or polynucleotides in combination with a known antigen, together with methods for using such compositions to induce or enhance protective immunity in a patient. In particular, the inventive compositions may be usefully employed in the treatment and/or prevention of disorders wherein stimulation of either a Th1-type or Th2-type immune response is beneficial to the reversal or prevention of the disorder. As used herein, a "patient" refers to any warm-blooded animal, preferably a human. Such a patient may be afflicted with disease or may be free of detectable disease. In other words, the inventive methods may be employed to induce protective immunity for the prevention or treatment of disease.

A composition of the present invention may also, or alternatively, contain a polynucleotide disclosed herein. Such polynucleotides may act directly as adjuvants; may encode one or more polypeptides that act as adjuvants, such that the polypeptide is generated in situ; or may be involved in a biosynthetic pathway that generates compounds with adjuvant activity. In such compositions, the polynucleotide may be present within any of a variety of delivery systems known to those of ordinary skill in the art, including nucleic acid expression systems, bacterial and viral expression systems. Appropriate nucleic acid expression systems contain the necessary DNA/RNA sequences for expression in the patient (such as a suitable promoter and terminator signal). Bacterial delivery systems involve the administration of a bacterium (such as Bacillus Calmette-Guerin) that expresses an immunogenic epitope of the polypeptide on its cell surface. In a preferred embodiment, the DNA and/or RNA may be introduced using a viral expression system (e.g., vaccinia or other poxvirus, retrovirus, or adenovirus), that may involve the use of a non-pathogenic, or defective, replication competent virus. Techniques for incorporating DNA and/or RNA into such expression systems are well known in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells. Methods for the administration of polynucleotide sequences comprising DNA and/or RNA include those disclosed in U.S. Pat. Nos. 5,580,859 and 5,589,466.

The compositions of the present invention preferably contain a physiologically acceptable carrier. While any suitable carrier known to those of ordinary skill in the art may be employed in the inventive compositions, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the compositions of this invention. Suitable biodegradable microspheres are disclosed, for example, in U.S. Pat. Nos. 4,897,268 and 5,075,109. The compositions of the present invention may also contain a substance designed to protect the antigen from rapid catabolism, such as aluminum hydroxide or mineral oil.

In general, the inventive compositions may be administered by injection (e.g., intradermal, intramuscular, intravenous or subcutaneous), intranasally (e.g., by aspiration) or orally. In certain embodiments, the compositions of the present invention are in a form suitable for delivery to the mucosal surfaces of the airways leading to or within the lungs. For example, the composition may be suspended in a liquid formulation for delivery to a patient in an aerosol form or by means of a nebulizer device similar to those currently employed in the treatment of asthma.

The preferred frequency of administration and effective dosage will vary both from individual to individual, and with the known antigen against which an immune response is to be raised, and may parallel those currently being used in immunization with the known antigen. In general, the amount of polypeptide immunostimulant present in a dose (or produced in situ by the polynucleotide in a dose) ranges from about 1 pg to about 100 mg per kg of host, typically from about 10 pg to about 1 mg, and preferably from about 100 pg to about 1 µg. Suitable dose sizes will vary with the size of the patient, but will typically range from about 0.1 ml to about 2 ml.

The word "about," when used in this application with reference to the amount of active component in a dose, contemplates a variance of up to 5% from the stated amount.

The following examples are offered by way of illustration and are not limiting.

EXAMPLE 1

IMMUNOSTIMULANT PROPERTIES OF *M. VACCAE* AND *M. SMEGMATIS*

The ability of heat-killed *M. vaccae* and heat-killed *M. smegmatis* to act as Th1 and/or Th2 immunostimulants was examined using the OVA-TCR adjuvant assay. This assay measures an antigen-specific immune response when an antigen, namely ovalbumin (OVA), and an immune response amplifier, or adjuvant, are co-injected into mice. The antigen-specific response is monitored by measuring the cytokine production of lymph node cells from immunized mice upon in vitro re-stimulation by specific antigen. Generally, Th1 adjuvants, or immunostimulants, induce an increase of Th1 cytokine (IFN-γ) production. Th2 adjuvants induce an increase of Th2 cytokine (IL-4) production.

Heat-killed *M. vaccae* was prepared as follows. *M. vaccae* (ATCC Number 15483) was cultured in sterile Medium 90 (yeast extract, 2.5 g/l; tryptone, 5 g/l; glucose 1 g/l) at 37° C. The cells were harvested by centrifugation, and transferred into sterile Middlebrook 7H9 medium (Difco Laboratories, Detroit Mich.) with glucose at 37° C. for one day. The medium was then centrifuged to pellet the bacteria, and the culture filtrate removed. The bacterial pellet was resuspended in phosphate buffered saline at a concentration of 10 mg/ml, equivalent to $10^{10}$ *M. vaccae* organisms per ml. The cell suspension was then autoclaved for 15 min at 120° C.

Heat-killed *M. smegmatis* was prepared essentially as described above for heat-killed *M. vaccae*.

The production of IFN-γ and IL-4 in cultures of lymph node cells from OVA-transgenic TCR mice (Wellesley Hospital Research Institute, Toronto, Canada) was determined using an enzyme-linked immunosorbent assay (ELISA). Three OVA-TCR transgenic mice were immunized subcutaneously in the footpad with a mixture of 1 µg ovalbumin (OVA) and 1 µg heat-killed *M. vaccae* or 1 µg OVA and 1 µg heat-killed *M. smegmatis*. Control mice were immunized with OVA and PBS. After 9 days, mice were sacrificed and the popliteal lymph nodes removed. Lymph node cells were cultured in DMEM (Gibco BRL) supplemented with 2 mM L-glutamine, 1 mM sodium pyruvate, 0.77 mM L-asparagine, 0.2 mM L-arganine, 160 mM penicillin G, 70 mM dihydrostreptomycin sulfate, $5 \times 10^{-2}$ mM beta mercaptoethanol and 5% FCS (cDMEM), and re-stimulated with OVA-peptide (SEQ ID NO: 31) at a concentration of 0, 0.03, 0.3 or 3 µM. Cells were incubated at 37° C. in humidified air containing 5% $CO_2$. Supernatants were collected after three days and used in ELISA assays to determine the cytokines present in the supernatant.

IFN-γ production in lymph node cells was measured as follows. ELISA plates were coated with a rat monoclonal antibody directed to mouse IFN-γ (PharMingen, San Diego Calif.) by incubating the wells with 1 µg/ml antibody in phosphate-buffered saline (PBS) for 4 hours at 4° C. Wells were blocked with PBS containing 0.2% Tween 20 for 1 hour at room temperature. The plates were then washed four times in PBS/0.2% Tween 20, and samples diluted 1:2 in culture medium in the ELISA plates were incubated overnight at room temperature. The plates were again washed, and a biotinylated monoclonal rat anti-mouse IFN-γ serum (PharMingen, San Diego, Calif.), diluted to 1 jig/ml in PBS, was added to each well. The plates were then incubated for 1 hour at room temperature, washed, and horseradish peroxidase-coupled avidin A (Vector Laboratories, Burlingame, Calif.) was added at a 1:4,000 dilution in PBS. After 1 hour incubation at room temperature, the plates were washed and orthophenylenediamine (OPD) substrate added. The reaction was stopped after 10 min with 10% (v/v) HCl. The optical density (OD) was determined at 490 nm. Supernatants that resulted in both replicates giving an OD two-fold greater than the mean OD from cells cultured in medium alone were considered positive.

The production of IL-4 in cultures of lymph node cells from OVA-TCR transgenic mice immunized with a mixture of 1 µg ovalbumin and either 1 µg heat-killed *M. vaccae* or 1 µg heat-killed *M. smegmatis* was determined using an enzyme-linked immunosorbent assay (ELISA), essentially as described for the detection of IFN-γ. ELISA plates were coated with a rat monoclonal antibody directed to mouse IL-4 (Pharmingen) by incubating the wells with 1 μg/ml antibody in phosphate-buffered saline (PBS) for 4 hours at 4° C. The antibodies used for detection were biotinylated anti-IL-4 antibodies (PharMingen).

As shown in FIGS. 1A and B, heat-killed *M. vaccae* enhanced both IL-4 and IFN-γ production in OVA-TCR transgenic mice, whereas heat-killed *M. smegmatis* had little or no effect on the production of IL-4 and IFN-γ. These results demonstrate that heat-killed *M. vaccae* is able to enhance both the Th1 and Th2 immune response to ovalbumin, whereas heat-killed *M. smegmatis* has little or no adjuvant effect on the immune response to ovalbumin.

EXAMPLE 2

CLONING AND SELECTION OF M. VACCAE IMMUNE RESPONSE AMPLIFIERS

*M. vaccae* (ATCC Number 15483) was cultured in medium 90 (yeast extract, 2.5 g/l; tryptone, 5 g/l; glucose, 1 g/l) at 37° C. for four days. Genomic DNA was isolated from these cells following standard protocols and digested with restriction endonuclease Sau3AI under conditions that produced DNA fragments of approximately 2.5 kb. The fragments were purified using the QIAquick PCR clean-up system (Qiagen, Venlo, The Netherlands).

*M. vaccae* DNA fragments were cloned by ligation into the BamHI site of pOLYG, a modified version of p16RI plasmid (ATCC Number 87120) containing a pBluescript polylinker (Stratagene, La Jolla Calif.) inserted in the KpnI site. *M. smegmatis* transformants (MST) were prepared following electroporation of *M. smegmatis* with pOLYG plasmids containing *M. vaccae* DNA inserts. Replica lift master plates were made of *M. smegmatis* bacterial colonies transformed with the library constructs and stored. Pools of 12 colonies were constituted and allowed to grow overnight. Bacterial pellets were then weighed, re-suspended in PBS at 10 mg/ml and autoclaved prior to storage. The immunomodulatory properties of the pools of heat-killed MST were determined by lymph node cell assay. Specifically, the production of IFN-γ and IL-4 in cultures of lymph node cells from OVA-TCR transgenic mice primed with a mixture of 1 μg ovalbumin and 1 μg heat-killed MST was determined by ELISA as described above.

Figure 2:
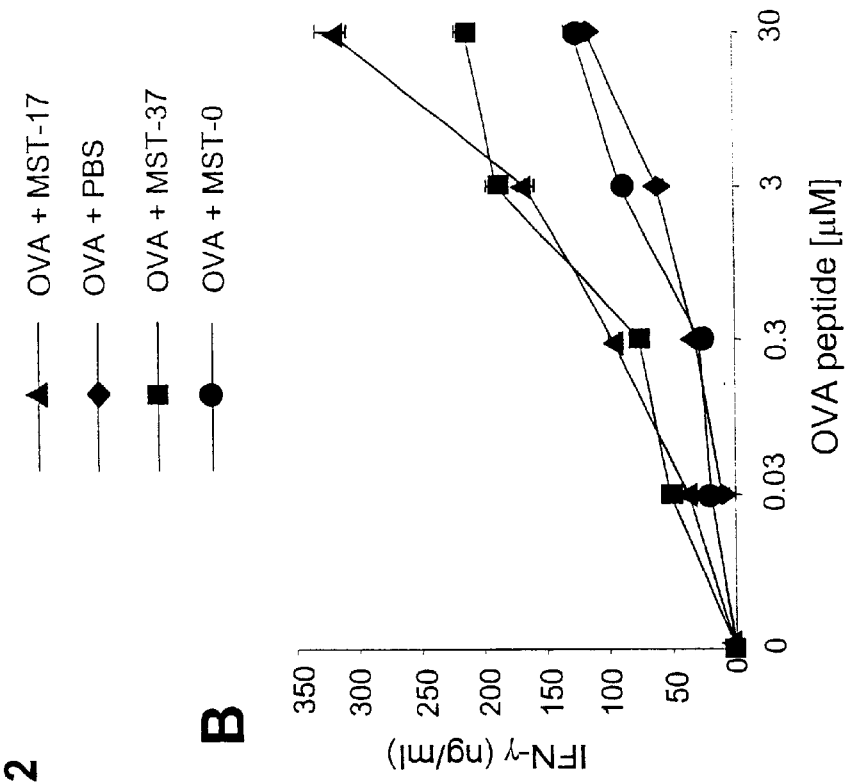
FIGS. 2A and B show IL-4 (FIG. 2A) and IFN-γ (FIG. 2B) production in OVA-TCR transgenic mice immunized with either OVA+heat-killed MST-17, OVA+heat-killed MST-37 or OVA+heat-killed MST-0. MST-0 is a control fraction of heat-killed *M. smegmatis* transformed with empty vector. Control mice were immunized with OVA+PBS.
Figure 2:
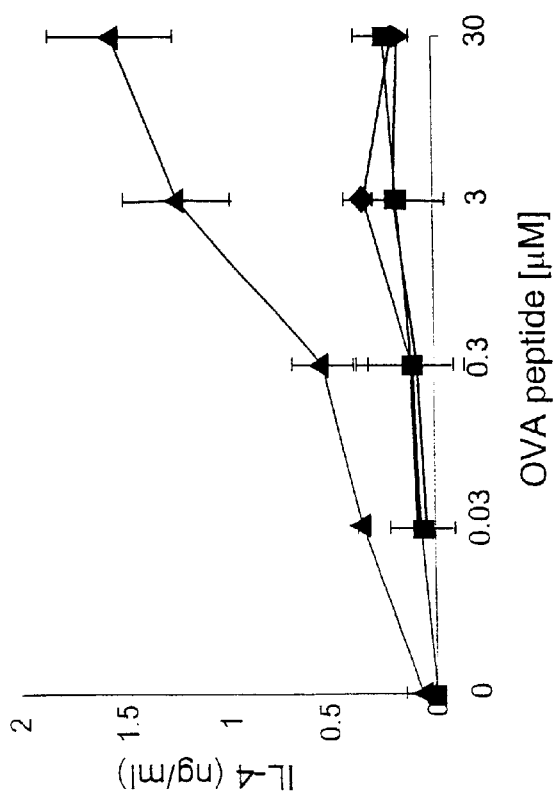

For MST pools that elicited a modified immune response (as determined by the ability to increase IFN-γ and/or IL-4 production in the lymph node cell assay), immunomodulatory properties of the individual members were subsequently tested using the lymph node cell assay. As shown in FIGS. 2A and B, two MST constructs, referred to as MST-17 and MST-37, were shown to modulate the immune response to ovalbumin. MST-17 was characterized as a Th2 adjuvant with a characteristic increase in IL-4 production, whereas MST-37 was characterized as a Th1 adjuvant since it stimulated the release of increased amounts of IFN-γ. The determined genomic DNA sequences of MST-17 and MST-37 are given in SEQ ID NO: 1 and 2, respectively.

These DNA sequences were compared to sequences in the EMBL DNA database Release 60, September 1999, and the SWISSPROT and TrEMBL databases updated to Oct. 20, 1999, using the FASTA and FASTX computer algorithms. MST-17 was found to contain a 420 bp insert derived from a single *M. vaccae* gene. MST-37 contained a longer insert (2,448 bp) which was found to include three *M. vaccae* genes, referred to as MST-37g1, MST-37g2 and MST-37g3.

Figure 3:
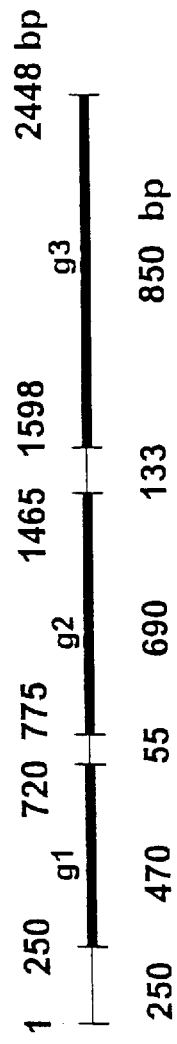
FIG. 3A is a schematic representations of the genomic organization of the insert of MST-37.
FIG. 3B is a comparison of the MST-37 construct with the homologous genomic DNA fragment from *M. tuberculosis*. The homologies shown in FIG. 3B were determined as described below FIG. 4 compares the production of IL4 by different sub-clones derived from MST-17. OVA-TCR transgenic mice were immunized with OVA+heat-killed MST-17RF1 or OVA+heat-killed MST-17RF3, or the controls OVA+heat-killed MST-0 and OVA+PBS.
Figure 3:
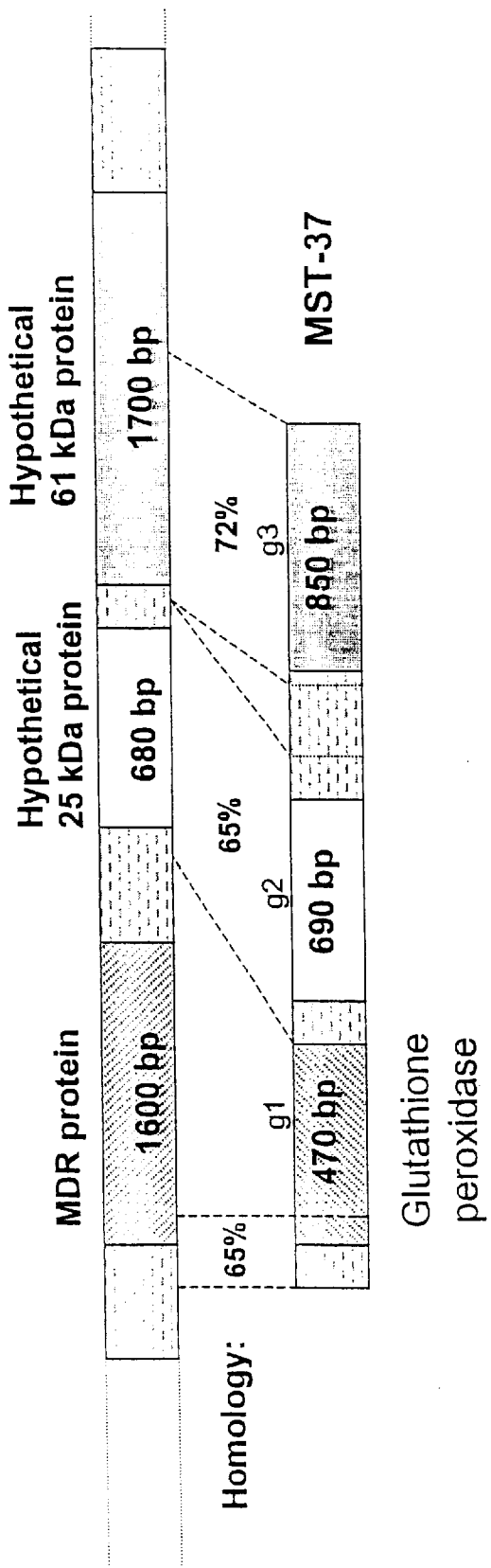

The determined nucleotide sequences of MST-37g1, MST-37g2 and MST-37g3 are given in SEQ ID NO: 3, 4 and 5, respectively. The genomic organization of the *M. vaccae* DNA insert in MST-37 and comparison of this MST-37 with the homologous region in the *M. tuberculosis* genome are given in FIGS. 3A and B, respectively. The predicted amino acid sequence of MST-17 (based on a database search and homology with *M. tuberculosis*-homologue) is given in SEQ ID NO: 6, with the predicted amino acid sequences of MST-37g1, MST-37g2 and MST-37g3 being given in SEQ ID NO: 7–9, respectively.

Each of the six possible reading frames of MST-17 (referred to as MST-17RF1 to MST-17RF6) and the three open reading frames identified in MST-37 was sub-cloned individually into a modified mycobacterial expression vector (MEV) for further identification of the active component (s). The modified vector was constructed to add a promoter region and His-tag motif in the cloning sites of pOLYG as follows. First, the promoter region of *M. tuberculosis* hsp65 gene (provided in SEQ ID NO: 10) was amplified with primers AD144 and AD 146 (SEQ ID NO: 13 and 14, respectively) and cloned into XbaI/BamHI-digested pOLYG to produce pOLYGhsp. This insert also provided two new restriction sites (PstI and SrfI). In a second step, a double-stranded oligonucleotide encoding a His-tag motif (provided in SEQ ID NO: 15) was prepared by ligation of primers AD148 and AD179 (SEQ ID NO: 11 and 12, respectively). This His-tag fragment was cloned into BamHI/ClaI-digested pOLYGhsp to produce pOLYGhsp/his. The 5' end of the His-tag sequence contained 2 additional restriction sites, EcoRV and HindIII. The pOLYGhsp/his mycobacterial expression vector therefore contained a linker between the hsp65 promoter and the His-tag that provided four new restriction sites for gene insertion.

Figure 4:
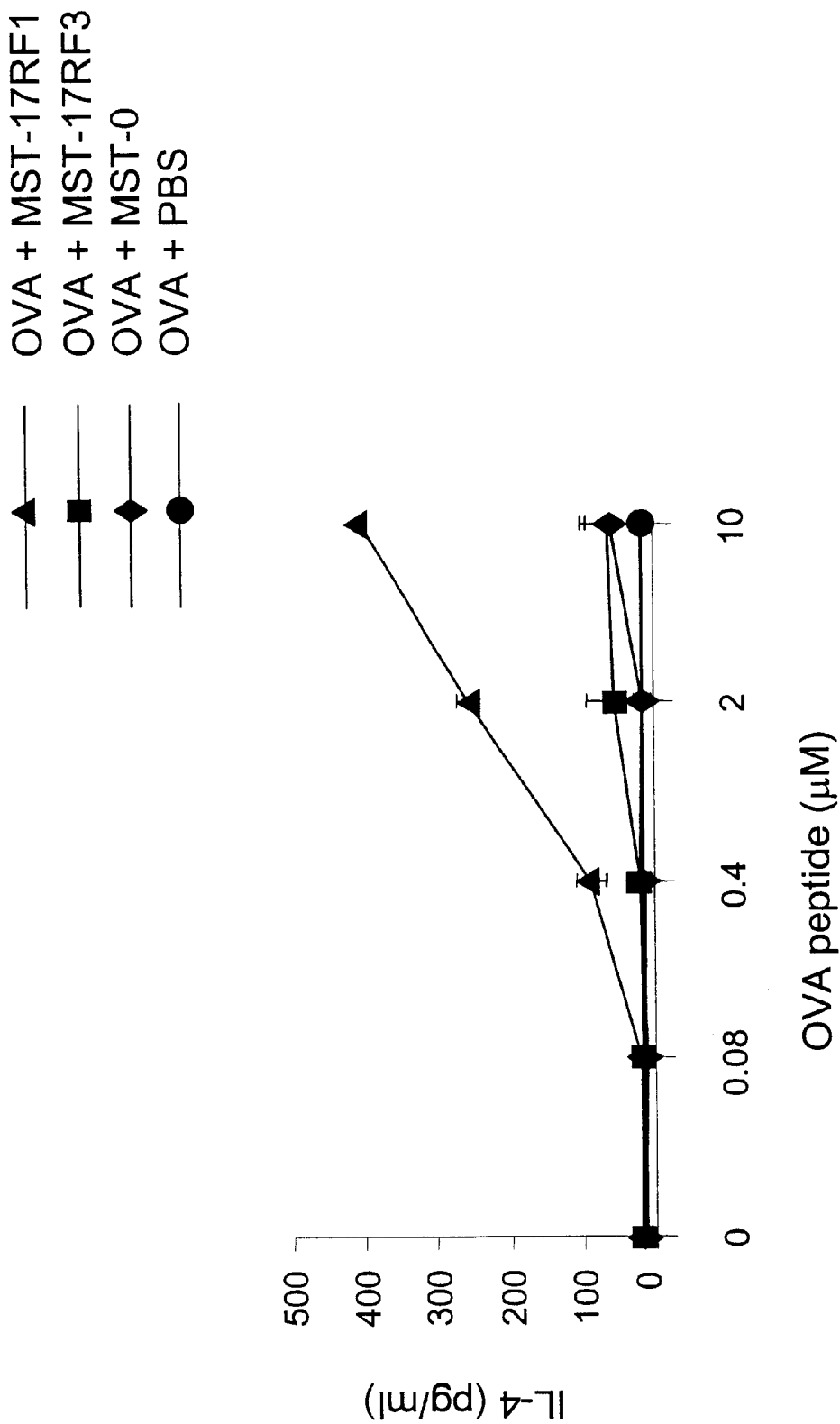

MST-17RF1, the only open reading frame in the MST-17 gene, was amplified with primers AD171 and AD172 (SEQ ID NO: 16 and 17, respectively). Digestion of the PCR product with HindIII produced a fragment with a 5' blunt-end and a 3' HindIII-compatible end. This DNA fragment was sub-cloned by ligation into pOLYGhsp/his digested with SrfI and HindIII. As shown in FIG. 4, MST-17RF1 stimulated the production of IL-4 in OVA-TCR transgenic mice in the lymph node cell assay described above, confirming that MST-17RF1 has Th2 adjuvant activity and that it is the active component of MST-17. MST-17RF3, which did not contain an open reading frame, was prepared using a PCR product generated with the primer pair AD171 and AD173 (SEQ ID NO: 16 and 18). MST-17RF3 was used as a control in this assay and showed no IL-4 stimulating activity (FIG. 4).

Figure 5:
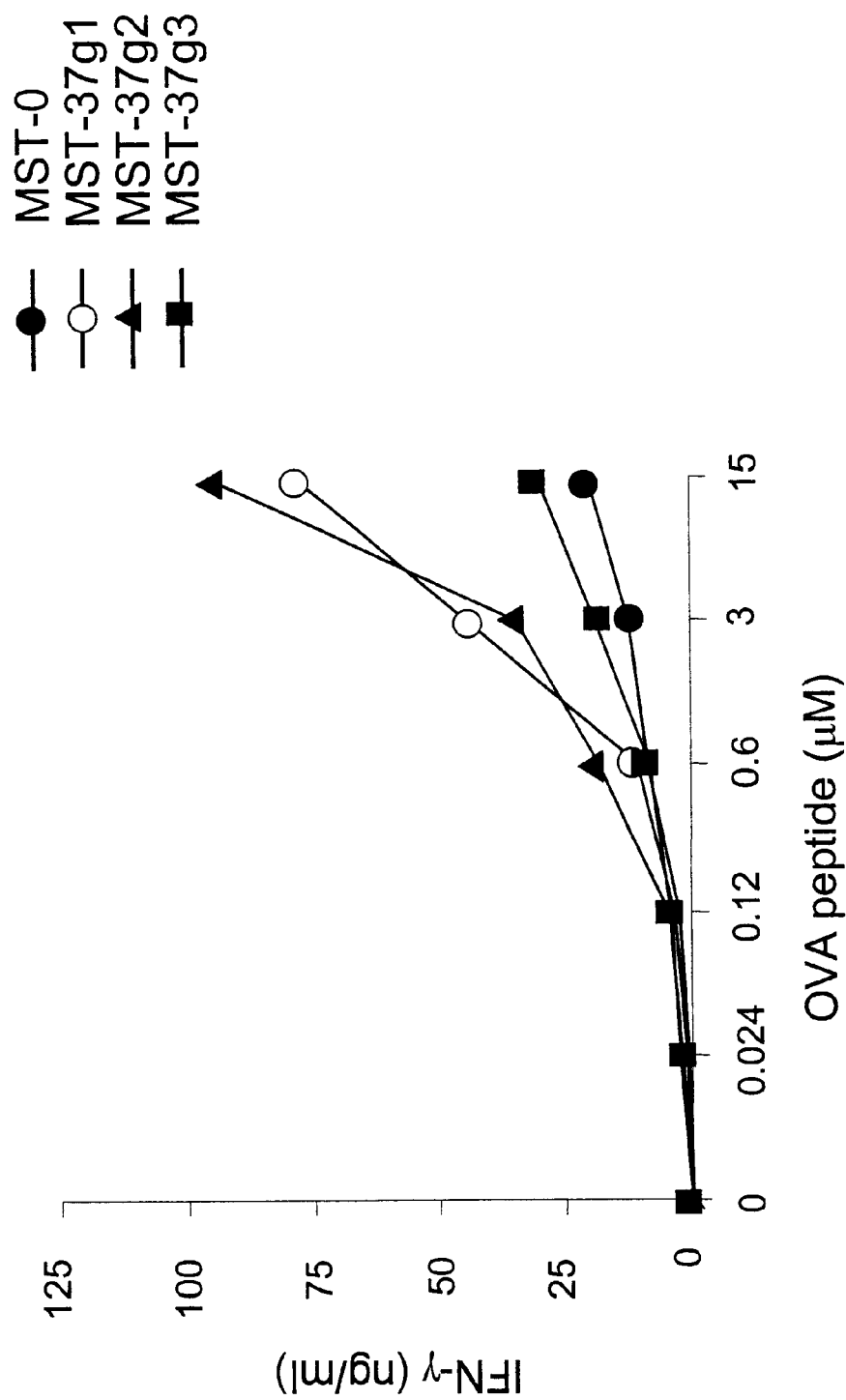
FIG. 5 compares the production of IFN-γ by different sub-clones derived from MST-37. OVA-TCR transgenic mice were immunized with OVA+heat-killed MST-37g1 (see FIG. 2), OVA+heat-killed MST-37g2 or OVA+heat-killed MST-37g3 or the controls OVA+heat-killed MST-0 and OVA+PBS.

Similarly, the three genes from MST-37 were amplified with the following primer pairs: AD213 and AD214 for MST-37g1 (SEQ ID NO: 19 and 20, respectively); AD215 and AD216 for MST-37g2 (SEQ ID NO: 21 and 22, respectively); and AD217 and AD218 for MST-37g3 (SEQ ID NO: 23 and 24, respectively). These PCR products were cloned individually into pOLYGhsp/his following the same procedure outlined above for MST-17RF1 subcloning. As shown in FIG. 5, MST-37g1 and MST-37g2 were found to display Th1 adjuvant activities in the OVA-TCR adjuvant model by stimulating IFN-γ production, suggesting that the products of MST-37g1 and MST-37g2 are the components of MST-37 with adjuvant activity.

EXAMPLE 3

ADJUVANT ACTIVITY OF RECOMBINANT MST CONSTRUCTS

The active components of MST-17 and MST-37 were subcloned into a vector for expression of recombinant polypeptides in bacterial cells. The bacterial expression vector was a modified pET16 vector (Novagen, Madison, Wis.). Inserts from pOLYGhsp/his MST-17 and MST-37 were amplified with the following primers pairs: AD266 and AD267 for MST-17RF1 (SEQ ID NO: 25 and 26, respectively); AD268 and AD275 for MST-37g1 (SEQ ID NO: 27 and 28, respectively); and AD270 and AD271 for MST-37g2 (SEQ ID NO: 29 and 30, respectively). The PCR products were cloned as EcoRI(BamHI fragments by ligation into the EcoRI/BamHI-digested pET16 vector. Competent BL21/DE3 cells were transformed with these constructs and induced to express recombinant protein by the addition of IPTG. Protein was purified from the bacterial culture using standard protocols.

Figure 6:
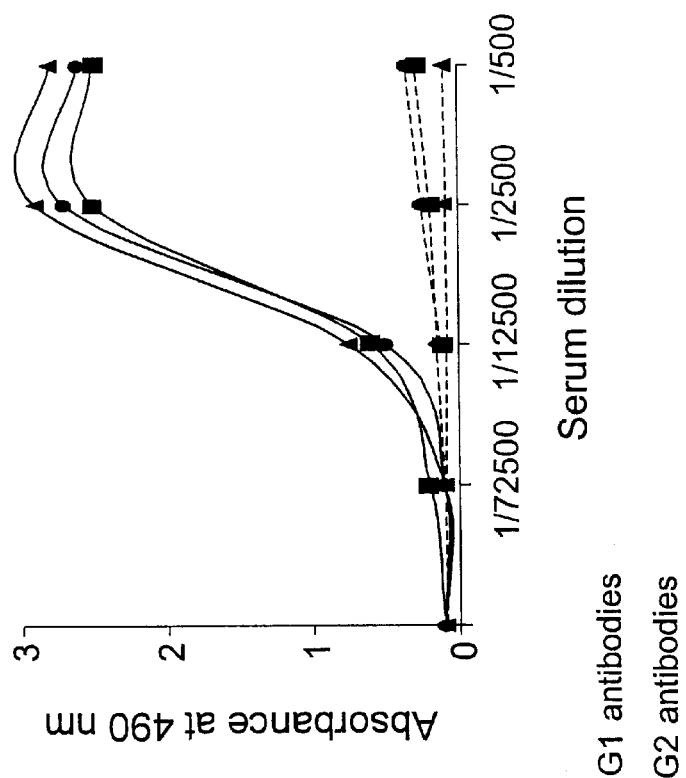
FIGS. 6A and B illustrate the production of anti-ovalbumin antibodies in three BALB/cByJ mice immunized with either OVA in IFA (FIG. 6A) or with OVA+MST-17RF1 in IFA (FIG. 6B).
Figure 6:
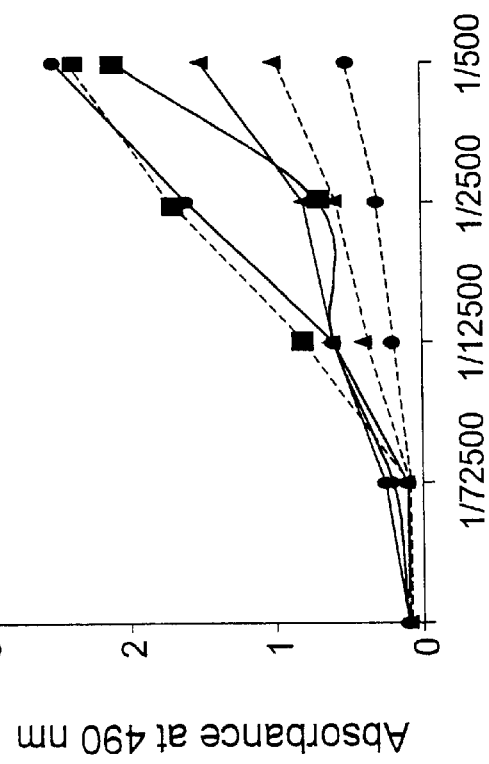

The antibody production induced by MST-17RF1 was examined by determining the titer and subclass of anti-OVA antibodies raised by injecting mice with OVA plus MST-17RF1. Specifically, three female BALB/cByJ mice were injected with 10 μg ovalbumin and 10 μg recombinant MST-17RF1 per mouse in Incomplete Freund's adjuvant (IFA). Control mice received 10 μg OVA in IFA. Injections were repeated three times at three week-intervals and blood samples were collected two weeks after the last injection. Sera were prepared according to standard procedures and the presence and subclass of anti-OVA antibodies was determined by ELISA as follows. The wells of a microtiter plate were coated with 500 ng of OVA. Antibody titres were measured by adding serial dilutions of serum into the wells. Bound antibodies were detected according to standard ELISA procedures. As shown in FIG. 6, the titers and subclasses of antibodies in control mice (immunized with OVA in IFA) were variable and low. In contrast, the titers of anti-OVA antibodies in the three mice that received OVA plus rMST-17RF1 in IFA were higher. The subclass of antibody raised in each of these three mice was IgG1. These results confirmed that MST-17RF1 is a Th2 immunostimulant, since induction of IgG1 antibodies is a characteristic of Th2 immune modulators.

Although the present invention has been described in some detail by way of illustration and example for purposes of clarity of understanding, changes and modifications can be carried out without departing from the scope of the invention which is intended to be limited only by the scope of the appended claims.

We claim:

1. An isolated polypeptide comprising SEQ ID NO: 8.

2. An isolated polypeptide comprising an amino acid sequence selected from the group consisting of:
   (a) sequences having at least 75% identity to SEQ ID NO: 8;
   (b) sequences having at least 90% identity to SEQ ID NO: 8; and
   (c) sequences having at least 95% identity to SEQ ID NO: 8,
wherein the polypeptide is capable of eliciting and/or enhancing an immune response.

3. An immunogenic composition comprising at least one polypeptide according to claim 2 and a heterologous antigen.

4. The immunogenic composition of claim 3, wherein the heterologous antigen is selected from the group consisting of: tumor-specific antigens, infectious disease antigens and autoantigens.

5. A fusion protein comprising at least one polypeptide according to claim 2 and a heterologous antigen.

6. The fusion protein of claim 5, wherein the heterologous antigen is selected from the group consisting of: tumor-specific antigens, infectious disease antigens and autoantigens.

7. An isolated polypeptide encoded by SEQ ID NO: 4.

8. An immunogenic composition comprising at least one polypeptide according to any one of claims 1 and 7 and a heterologous antigen.

9. The immunogenic composition of claim 8, wherein the heterologous antigen is selected from the group consisting of: tumor-specific antigens, infectious disease antigens and autoantigens.

10. A fusion protein comprising at least one polypeptide according to any one of claims 1 and 7 and a heterologous antigen.

11. The fusion protein of claim 10, wherein the heterologous antigen is selected from the group consisting of: tumor-specific antigens, infectious disease antigens and autoantigens.

* * * * *